(12) United States Patent
Yildirim et al.

(10) Patent No.: US 12,080,014 B2
(45) Date of Patent: Sep. 3, 2024

(54) VIRTUAL LIGAMENT BALANCING

(71) Applicant: Howmedica Osteonics Corp., Mahwah, NJ (US)

(72) Inventors: Gokce Yildirim, Weehawken, NJ (US); Sally Liarno, Bergenfield, NJ (US); Mark Gruczynski, Kinnelon, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 0 days.

(21) Appl. No.: 17/953,737

(22) Filed: Sep. 27, 2022

(65) Prior Publication Data

US 2023/0025727 A1 Jan. 26, 2023

Related U.S. Application Data

(60) Continuation of application No. 17/024,896, filed on Sep. 18, 2020, now Pat. No. 11,484,251, which is a division of application No. 16/211,706, filed on Dec. 6, 2018, now Pat. No. 10,827,971.

(60) Provisional application No. 62/608,050, filed on Dec. 20, 2017.

(51) Int. Cl.
*G06T 7/60* (2017.01)
*G06T 7/00* (2017.01)

(52) U.S. Cl.
CPC .............. *G06T 7/60* (2013.01); *G06T 7/0014* (2013.01); *G06T 2207/30008* (2013.01)

(58) Field of Classification Search
None
See application file for complete search history.

(56) References Cited

U.S. PATENT DOCUMENTS

| | | | |
|---|---|---|---|
| 6,224,373 B1 | 5/2001 | Lee et al. | |
| 6,315,445 B1 | 11/2001 | Mazess et al. | |
| 7,831,292 B2 | 11/2010 | Quaid et al. | |
| 8,095,200 B2 | 1/2012 | Quaid, III | |
| 8,617,171 B2 | 12/2013 | Park et al. | |
| 9,285,788 B2 | 3/2016 | Nicoletti et al. | |
| 2002/0065528 A1 | 5/2002 | Clark et al. | |
| 2006/0161052 A1 | 7/2006 | Colombet et al. | |
| 2007/0219561 A1 | 9/2007 | Lavallee et al. | |

(Continued)

OTHER PUBLICATIONS

Siebert, Werner, et al. "Technique and first clinical results of robot-assisted total knee replacement." The Knee 9.3 (2002): 173-180. (Year: 2002).*

(Continued)

*Primary Examiner* — Michelle M Entezari Hausmann
(74) *Attorney, Agent, or Firm* — Lerner David LLP

(57) ABSTRACT

A method of generating a correction plan for a knee of a patient includes obtaining a ratio of reference bone density to reference ligament tension in a reference population. A bone of the knee of the patient may be imaged. From the image of the bone, a first dataset may be determined including at least one site of ligament attachment and existing dwell points of a medial femoral condyle and lateral femoral condyle of the patient on a tibia of the patient. Desired positions of contact in three dimensions of the femoral condyles of the patient with the tibia of the patient may be obtained by determining a relationship in which a ratio of bone density to ligament tension of the patient is substantially equal to the ratio of reference bone density to reference ligament tension.

10 Claims, 13 Drawing Sheets

(56) References Cited

U.S. PATENT DOCUMENTS

| | | | |
|---|---|---|---|
| 2008/0294269 A1 | 11/2008 | Fell | |
| 2010/0016978 A1 | 1/2010 | Williams et al. | |
| 2010/0016979 A1 | 1/2010 | Wyss et al. | |
| 2012/0290088 A1 | 11/2012 | Amirouche et al. | |
| 2013/0004043 A1 | 1/2013 | Ross et al. | |
| 2013/0144385 A1 | 6/2013 | Vowles | |
| 2013/0317511 A1* | 11/2013 | Bojarski | A61B 17/1764 606/102 |
| 2014/0228860 A1* | 8/2014 | Steines | A61B 34/10 606/130 |
| 2014/0270444 A1 | 9/2014 | Yang et al. | |
| 2015/0032215 A1 | 1/2015 | Slamin et al. | |
| 2015/0080717 A1 | 3/2015 | Ferko | |
| 2015/0105698 A1 | 4/2015 | Park | |
| 2015/0119987 A1 | 4/2015 | Davignon et al. | |
| 2015/0148807 A1 | 5/2015 | Park | |
| 2016/0045317 A1* | 2/2016 | Lang | A61F 2/30942 700/98 |
| 2016/0310279 A1 | 10/2016 | Samuelson et al. | |
| 2017/0079801 A1 | 3/2017 | Drury et al. | |
| 2017/0162078 A1 | 6/2017 | Imhauser et al. | |
| 2017/0181755 A1 | 6/2017 | Librot | |
| 2017/0189119 A1 | 7/2017 | Yildirim et al. | |
| 2017/0258526 A1* | 9/2017 | Lang | A61B 17/155 |
| 2019/0175278 A1 | 6/2019 | Zhang | |
| 2020/0030034 A1 | 1/2020 | Kontaxis et al. | |
| 2020/0163722 A1 | 5/2020 | Yildirim et al. | |

OTHER PUBLICATIONS

Liu, Hao, et al. "Changes in local bone mineral density can guide the treatment plan for patients with rupture of the anterior cruciate ligament." Annals of Palliative Medicine 10.6 (2021): 6388398-6386398. (Year: 2021).*

Roth, Tabitha, et al. "An automated optimization pipeline for clinical-grade computer-assisted planning of high tibial osteotomies under consideration of weight-bearing." Computer Assisted Surgery 28.1 (2023): 2211728. (Year: 2023).*

Ho, Jiahui. "The development of an integrated computer based system for knee joint related clinical diagnosis, pre-surgical planning and post-operative monitoring." PhD diss., 2010. (Year: 2010).*

Kim, Du-Han, et al. "Two-stage revision anterior cruciate ligament reconstruction." Knee Surgery & Related Research 31 (2019): 1-6. (Year: 2019).*

Piccolo, Claudia Lucia, et al. "Imaging of knee osteoarthritis: a review of multimodal diagnostic approach." Quantitative Imaging in Medicine and Surgery 13.11 (2023): 7582. (Year: 2023).*

Emovi, KneeKG Product Brochure, Innovative 3DKnee Function Assessment Device, 2012.

Wroble, R. R., et al., Repeatability of the KT-1000 arthrometer in a normal population, The American Journal of Sports Medicine, vol. 18, No. 4, 1990 American Orthopaedic Society for Sports Medicine.

Extended European Search Report for Application No. 17150450.9 dated Apr. 21, 2017.

Wing Hung Alex NG, et al., "Imaging of the anterior cruciate ligament"?World Journal of Orthopedics, Jan. 2011 , p. 75, vol. 2, No. 8.

B.L. Van Meer, et al., "Bone mineral density changes in the knee following anterior cruciate ligament rupture"? Osteoarthritis and Cartilage., Jan. 2014, pp. 154-161, vol. 22, No. 1.

Seim, Heiko, et al. "Segmentation of bony structures with ligament attachment sites." Bildverarbeitung für die Medizin 2008. Springer, Berlin, Heidelberg, Apr. 2008, pp. 207-211.

Extended European Search Report including the Written Opinion for Application No. EP 18213759.6 dated May 28, 2019.

Cyr, A.J., Shalhoub, S.S., Fitzwater, F.G., Ferris, L. A., & Maletsky, L.P. (2015). Mapping of Contributions From Collateral Ligaments to Overall Knee Joint Constraint: An Experimental Cadaveric Study. Journal of Biomechanical Engineering , 137(6). (Year: 2015).

Eng, Carolyn M., Francesco Q. Pancheri, Daniel E. Lieberman, Andrew A. Biewener, and Luis Dorfmann, "Directional differences in the biaxial material properties of fascia lata and the implications for fascia function." Annals of biomedical engineering 42, No. 6 (2014): 1224-1237. (Year: 2014).

* cited by examiner

| Patient ID | Anterior Max | Posterior Max | Tubercle | | P/A ratio | T/A ratio | P/T ratio |
|---|---|---|---|---|---|---|---|
| 1 | 757 | 1126 | 722 | | 1.49 | 0.95 | 1.56 |
| 2 | 780 | 1212 | 730 | | 1.55 | 0.94 | 1.66 |
| 3 | 908 | 1500 | 1341 | | 1.65 | 1.48 | 1.12 |
| 4 | 1064 | 1328 | 1136 | | 1.25 | 1.07 | 1.17 |
| 5 | 953 | 1340 | 909 | | 1.41 | 0.95 | 1.47 |
| 6 | 711 | 993 | 960 | | 1.40 | 1.35 | 1.03 |
| 7 | 1063 | 1132 | 1254 | | 1.06 | 1.18 | 0.90 |
| 8 | 903 | 1189 | 1228 | | 1.32 | 1.36 | 0.97 |
| 9 | 1006 | 1191 | 868 | | 1.18 | 0.86 | 1.37 |
| 10 | 538 | 1210 | 625 | | 2.25 | 1.16 | 1.94 |
| 11 | 692 | 1329 | 625 | | 1.92 | 0.90 | 2.13 |
| 12 | 830 | 1273 | 944 | | 1.53 | 1.14 | 1.35 |
| 13 | 527 | 993 | 625 | | 1.88 | 1.19 | 1.59 |
| 14 | 1280 | 1384 | 1277 | | 1.08 | 1.00 | 1.08 |
| 15 | 978 | 1245 | 1100 | | 1.27 | 1.12 | 1.13 |
| 16 | 824 | 1160 | 971 | | 1.41 | 1.18 | 1.19 |
| 17 | 1054 | 1271 | 842 | | 1.21 | 0.80 | 1.51 |
| 18 | 717 | 1275 | 1016 | | 1.78 | 1.42 | 1.25 |
| 19 | 1095 | 1014 | 873 | | 0.93 | 0.80 | 1.16 |
| 20 | 304 | 908 | 345 | | 2.99 | 1.13 | 2.63 |
| | | | | Average | 1.53 | 1.02 | 1.49 |
| | | | | SD | 0.52 | 0.14 | 0.44 |
| | | | High Ratio | Average | 1.54 | 1.40 | 1.09 |
| | | | | SD | 0.22 | 0.06 | 0.12 |

*FIG. 8*

| Patient ID | Anterior Max | Posterior Max | Tubercle | | P/A ratio | T/A ratio | P/T ratio |
|---|---|---|---|---|---|---|---|
| 21 | 882 | 1047 | 869 | | 1.19 | 0.99 | 1.20 |
| 22 | 897 | 1264 | 1203 | | 1.41 | 1.34 | 1.05 |
| 23 | 941 | 1055 | 1097 | | 1.12 | 1.17 | 0.96 |
| 24 | 819 | 1227 | 1072 | | 1.50 | 1.31 | 1.14 |
| 25 | 899 | 1104 | 733 | | 1.23 | 0.82 | 1.51 |
| 26 | 934 | 1322 | 916 | | 1.42 | 0.98 | 1.44 |
| 27 | 927 | 1147 | 858 | | 1.24 | 0.93 | 1.34 |
| 28 | 1098 | 1482 | 1077 | | 1.35 | 0.98 | 1.38 |
| 29 | 887 | 997 | 923 | | 1.12 | 1.04 | 1.08 |
| 30 | 933 | 950 | 1073 | | 1.02 | 1.15 | 0.89 |
| 31 | 997 | 1155 | 1155 | | 1.16 | 1.16 | 1.00 |
| 32 | 821 | 947 | 969 | | 1.15 | 1.18 | 0.98 |
| 33 | 1413 | 1201 | 1406 | | 0.85 | 1.00 | 0.85 |
| 34 | 684 | 1053 | 570 | | 1.54 | 0.83 | 1.85 |
| 35 | 655 | 1112 | 823 | | 1.70 | 1.26 | 1.35 |
| 36 | 844 | 1356 | 1055 | | 1.61 | 1.25 | 1.29 |
| 37 | 826 | 1003 | 1133 | | 1.21 | 1.37 | 0.89 |
| 38 | 711 | 752 | 737 | | 1.06 | 1.04 | 1.02 |
| 39 | 574 | 862 | 620 | | 1.50 | 1.08 | 1.39 |
| 40 | 578 | 781 | 625 | | 1.35 | 1.08 | 1.25 |
| 41 | 794 | 896 | 1069 | | 1.12 | 1.35 | 0.83 |
| 42 | 733 | 860 | 850 | | 1.17 | 1.16 | 1.01 |
| 43 | 916 | 962 | 939 | | 1.05 | 1.03 | 1.02 |
| 44 | 1002 | 906 | 1059 | | 0.90 | 1.06 | 0.86 |
| 45 | 969 | 1034 | 970 | | 1.07 | 1.00 | 1.07 |
| 46 | 756 | 996 | 863 | | 1.32 | 1.14 | 1.15 |
| 47 | 819 | 1049 | 825 | | 1.28 | 1.01 | 1.27 |
| 48 | 700 | 661 | 640 | | 0.94 | 0.91 | 1.03 |
| 49 | 818 | 1009 | 1340 | | 1.23 | 1.64 | 0.75 |
| 50 | 567 | 1004 | 881 | | 1.77 | 1.55 | 1.14 |
| 51 | 871 | 1116 | 1363 | | 1.28 | 1.55 | 0.82 |
| 52 | 520 | 872 | 636 | | 1.68 | 1.22 | 1.37 |
| 53 | 736 | 888 | 1110 | | 1.21 | 1.51 | 0.80 |
| | | | | Average | 1.18 | 1.03 | 1.16 |
| | | | | SD | 0.18 | 0.10 | 0.25 |
| | | | High Ratio | Average | 1.43 | 1.40 | 1.04 |
| | | | | SD | 0.23 | 0.14 | 0.23 |

*FIG. 9*

| Patient ID | Anterior Max | Posterior Max | Tubercle | | P/A ratio | T/A ratio | P/T ratio |
|---|---|---|---|---|---|---|---|
| 54 | 902 | 1341 | 911 | | 1.49 | 1.01 | 1.47 |
| 55 | 894 | 1025 | 955 | | 1.15 | 1.07 | 1.07 |
| 56 | 976 | 1007 | 967 | | 1.03 | 0.99 | 1.04 |
| 57 | 815 | 892 | 709 | | 1.09 | 0.87 | 1.26 |
| 58 | 736 | 1285 | 861 | | 1.75 | 1.17 | 1.49 |
| 59 | 900 | 1120 | 914 | | 1.24 | 1.02 | 1.23 |
| 60 | 830 | 1175 | 919 | | 1.42 | 1.11 | 1.28 |
| 61 | 824 | 1036 | 1087 | | 1.26 | 1.32 | 0.95 |
| 62 | 617 | 1166 | 754 | | 1.89 | 1.22 | 1.55 |
| 63 | 802 | 1110 | 754 | | 1.38 | 0.94 | 1.47 |
| 64 | 838 | 1066 | 917 | | 1.27 | 1.09 | 1.16 |
| 65 | 851 | 1214 | 1071 | | 1.43 | 1.26 | 1.13 |
| | | | | Average | 1.31 | 1.03 | 1.28 |
| | | | | SD | 0.22 | 0.09 | 0.17 |
| | | | | High Ratio Average | 1.52 | 1.27 | 1.21 |
| | | | | SD | 0.33 | 0.05 | 0.30 |

*FIG. 10*

| Patient ID | Anterior Max | Posterior Max | Tubercle | | P/A ratio | T/A ratio | P/T ratio |
|---|---|---|---|---|---|---|---|
| 66 | 700 | 1078 | 743 | | 1.54 | 1.06 | 1.45 |
| 67 | 1076 | 1100 | 1046 | | 1.02 | 0.97 | 1.05 |
| 68 | 749 | 1278 | 778 | | 1.71 | 1.04 | 1.64 |
| 69 | 729 | 1146 | 928 | | 1.57 | 1.27 | 1.23 |
| 70 | 848 | 919 | 728 | | 1.08 | 0.86 | 1.26 |
| 71 | 766 | 979 | 760 | | 1.28 | 0.99 | 1.29 |
| 72 | 724 | 789 | 895 | | 1.09 | 1.24 | 0.88 |
| 73 | 656 | 830 | 662 | | 1.27 | 1.01 | 1.25 |
| | | | | Average | 1.32 | 0.99 | 1.32 |
| | | | | SD | 0.26 | 0.07 | 0.20 |
| | | | High Ratio | Average | 1.33 | 1.25 | 1.06 |
| | | | | SD | 0.34 | 0.03 | 0.25 |

*FIG. 11*

VIRTUAL LIGAMENT BALANCING

CROSS-REFERENCE TO RELATED APPLICATIONS

This application is a continuation of U.S. patent application Ser. No. 17/024,896, filed Sep. 18, 2020, which is a divisional of U.S. patent application Ser. No. 16/211,706, filed Dec. 6, 2018, now U.S. Pat. No. 10,827,971, issued on Nov. 10, 2020, which claims priority to the filing date of U.S. Provisional Patent Application No. 62/608,050, filed Dec. 20, 2017, the disclosures of which are hereby incorporated by reference herein.

BACKGROUND OF THE DISCLOSURE

During a typical knee replacement procedure, a surgeon removes a portion of one or more diseased portions of the bones forming the knee joint, such as the distal femur and the proximal tibia, and one or more prosthetic components are installed onto the prepared bone in order to restore proper knee functioning. The success of a knee replacement procedure, such as a total knee replacement ("TKR"), a unicondylar knee replacement ("UKR"), or a bi-cruciate retaining knee replacement ("BCR"), may be dependent upon proper soft tissue balancing, which may also be referred to as ligament balancing or gap balancing. Proper ligament balancing may in turn be dependent upon the size and placement of the prosthetic components, as well as the functioning of the remaining soft tissues affecting the joint.

Traditionally, soft tissue balancing is performed intraoperatively. For example, in a traditional TKR procedure, a surgeon creates a planar cut into the proximal tibia and a plurality of planar cuts into the distal tibia, the re-surfaced native bones being adapted to mate with corresponding surfaces on the prosthetic tibial component and the prosthetic femoral component. After preparation of the bones, and prior to implanting the prosthetic components onto the bones, trial components are coupled to the bones. With the trial components coupled to the bones, the knee may be taken through a range of flexion to determine if the knee is properly stabilized by the trial components and the remaining soft tissue. For example, the surgeon may measure the flexion gap when the knee is in flexion at 90 degrees, and the extension gap when the knee is in extension at 0 degrees, with the goal of having equal gaps in flexion and extension. Gap balancing may be performed by various techniques, such as measured resection. If the trial components do not provide acceptable results, the surgeon may intraoperatively alter the surgical plan in an attempt to achieve proper gap balancing. Alterations to the surgical plan may include performing soft tissue release and/or creating additional cuts in the proximal tibia and/or distal femur to change the orientation of the prosthetic components and/or to increase spacing between the bones. Once the surgeon determines that the trial components provide acceptable knee functionality, the trial components are removed and the final prosthetic components are implanted onto the bone(s).

One potential drawback of the traditional method of gap balancing is that it only takes into account the flexion gap and extension gap, without taking into account mid-flexion laxity. Another potential drawback is that the gap balancing is performed only after initial cuts are made, and further corrective procedures must be performed intra-operatively by the surgeon on the spot.

In view of the goals of gap balancing and the drawbacks of the traditional methods, it would be preferable to be able to perform "virtual" gap balancing pre-operatively, so that the prosthetic implants and their placement on the bone prior to beginning the surgery.

BRIEF SUMMARY

According to one aspect of the disclosure, a method of generating a correction plan for a knee of a patient includes obtaining a ratio of reference bone density to reference ligament tension in a reference population. A bone of the knee of the patient may be imaged. From the image of the bone, a first dataset may be determined including at least one site of ligament attachment and existing dwell points of a medial femoral condyle and lateral femoral condyle of the patient on a tibia of the patient. Desired positions of contact in three dimensions of the femoral condyles of the patient with the tibia of the patient may be obtained by determining a relationship in which a ratio of bone density to ligament tension of the patient is substantially equal to the ratio of reference bone density to reference ligament tension.

The relationship may include balancing vertical forces acting on the knee of the patient, and/or balancing horizontal forces acting on the knee of the patient, and/or balancing moments acting on the knee of the patient. The reference population may comprise a group of individuals having a parameter in common with the patient, and the parameter may be selected from the group consisting of sex, age, and race. The ratio of reference bone density to reference ligament tension in the reference population may be obtained by comparing (i) at least one bone density ratio of at least one reference knee of at least one reference individual in the reference population to (ii) at least one ligament tension of the at least one reference knee of the at least one reference individual in the reference population. The ligament tension may be determined with a dial test. The reference population may include a plurality of reference individuals with healthy knee joints.

According to another aspect of the disclosure, a method of predicting an amount of laxity in a knee ligament includes imaging a knee of a patient to produce a plurality of image layers, each image layer being a transverse cross-section of the knee spaced apart a distance from an adjacent layer. The method includes determining a position of maximum bone density in each of the plurality of image layers, the position of maximum bone density being associated with the knee ligament. The method also includes determining a directionality of the positions of maximum bone density in the plurality of image layers, and predicting the amount of laxity in the knee ligament based on the directionality of the positions of maximum bone density in the plurality of image layers. Determining the directionality of the positions of maximum bone density in the plurality of image layers may include creating a line representing the directionality on the plurality of image layers. The line may be a best-fit straight line. Predicting the amount of laxity may include predicting a relatively stiff ligament when the directionality is relatively vertically aligned with a mechanical axis of the tibia, and predicting a relatively loose ligament when the directionality points in a relatively anterior direction.

BRIEF DESCRIPTION OF THE DRAWINGS

FIG. 8 is a table of calculated density ratios for Caucasian males expected to have healthy knee joints.

FIG. 9 is a table of calculated density ratios for Caucasian females expected to have healthy knee joints.

FIG. 10 is a table of calculated density ratios for Asian males expected to have healthy knee joints.

FIG. 11 is a table of calculated density ratios for Asian females expected to have healthy knee joints.

DETAILED DESCRIPTION

Body tissues, such as ligaments, tendons, muscles, and fibrocartilage, may affect how one body portion, such as a bone of a joint, interacts with another body portion, such as another bone of the joint. Generally, if a bone or a portion of a bone undergoes frequent loading, the density of the portion of the bone loaded may be generally greater than surrounding bone that undergoes less loading.

Figure 1:
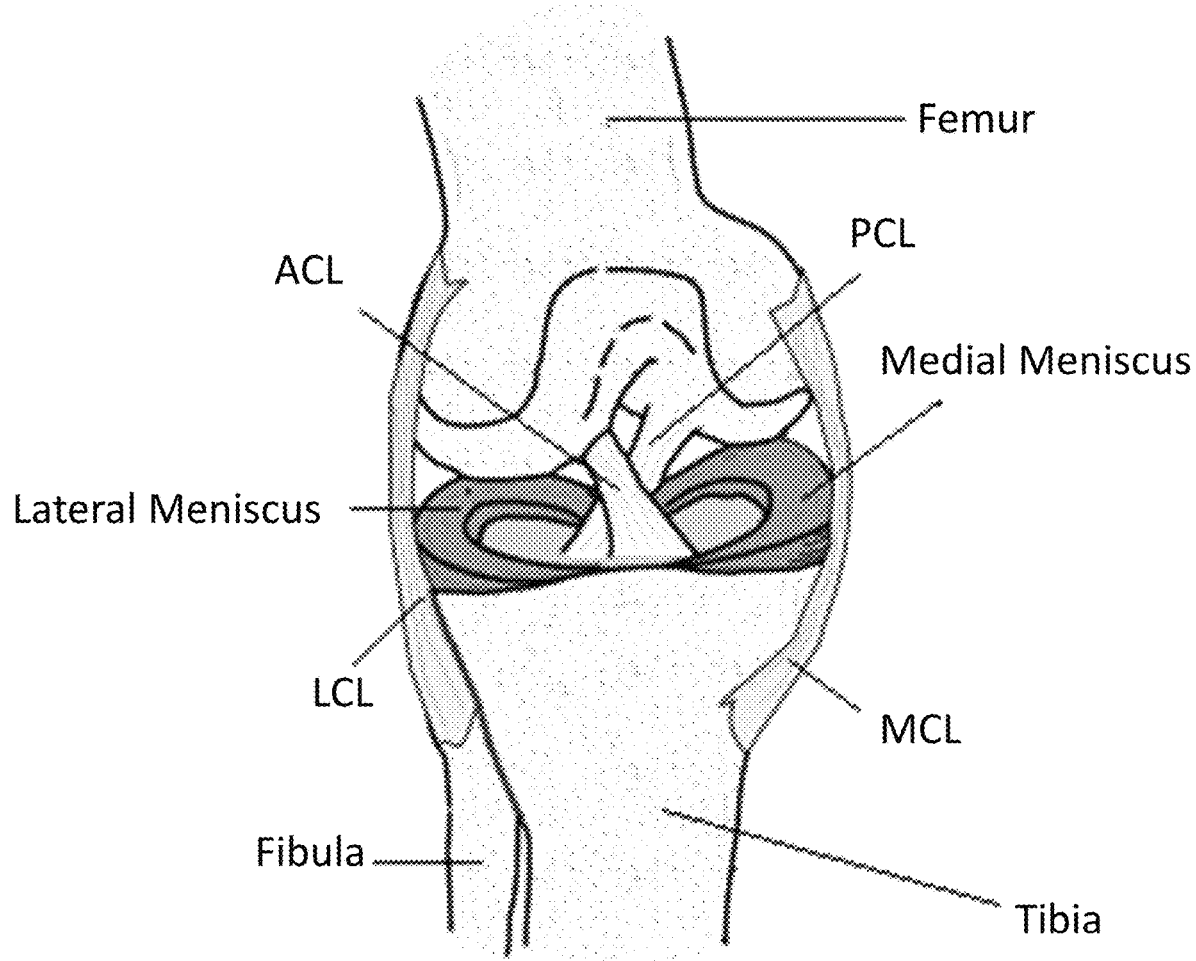
FIG. 1 is a schematic drawing of certain components of a knee joint.

FIG. 1 is a highly simplified illustration of a typical right knee joint of a patient. The medial and lateral condyles of the distal femur articulate with respect to the medial and lateral condyles of the tibia, respectively. The articulation of the femur against the tibia is facilitated by cartilaginous tissue including the medial meniscus, which is attached the medial condyle of the tibia, and the lateral meniscus, which is attached to the lateral condyle of the tibia.

Still referring to FIG. 1, the knee joint is stabilized, in part, by four main ligaments. The anterior cruciate ligament ("ACL") connects the femur to the tibia, starting from the posteromedial aspect of the lateral femoral condyle and extending in an anteromedial direction to its point of attachment at the anteromedial aspect of the tibia. The ACL crosses the posterior cruciate ligament ("PCL") and prevents anterior translation and excess rotation of the tibia with respect to the femur. The PCL, on the other hand, connects the posterior intercondylar area of the tibia to the medial condyle of the femur and helps to resist posterior translation of the tibia with respect to the femur. The other major ligaments of the knee include the medial collateral ligament ("MCL") which attaches the medial epicondyle of the femur to the medial condyle of the tibia and resists valgus forces on the knee, and the lateral collateral ligament ("LCL") which attaches the lateral epicondyle of the femur to the head of the fibula and resists *varus* forces on the knee. The ACL includes two principal fiber bundles, including the anteromedial ("AM") bundle and the posterolateral ("PL") bundle. The AM bundle is tense when the knee is flexed, and helps the knee limit anterior tibial translation when the knee is flexed. The PL bundle is tense when the knee is in extended, and helps the knee limit anterior tibial translation, hyperextension, and rotation.

Figure 2:
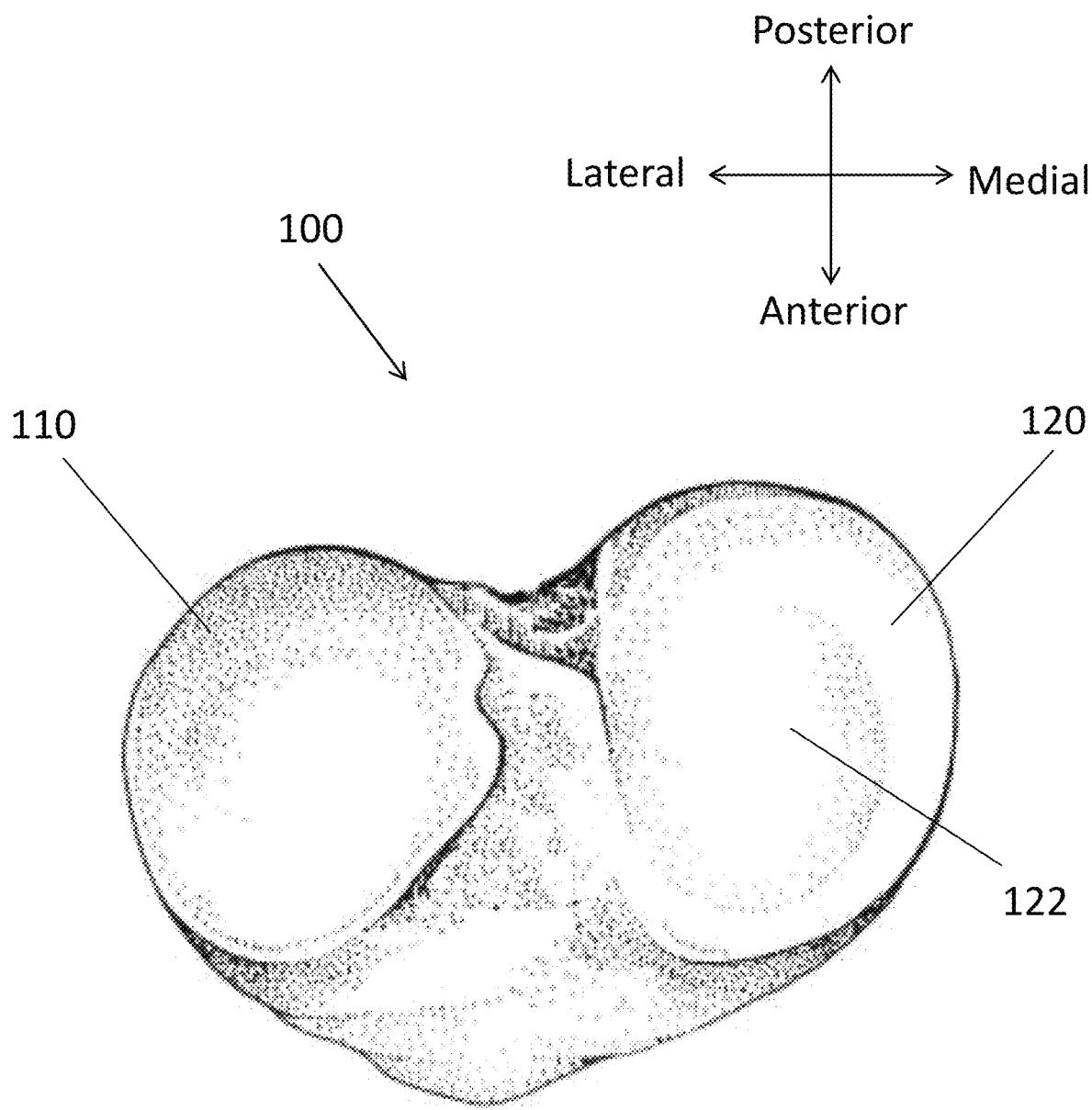
FIG. 2 is a schematic top view of a tibia of a healthy knee.
Figure 3:
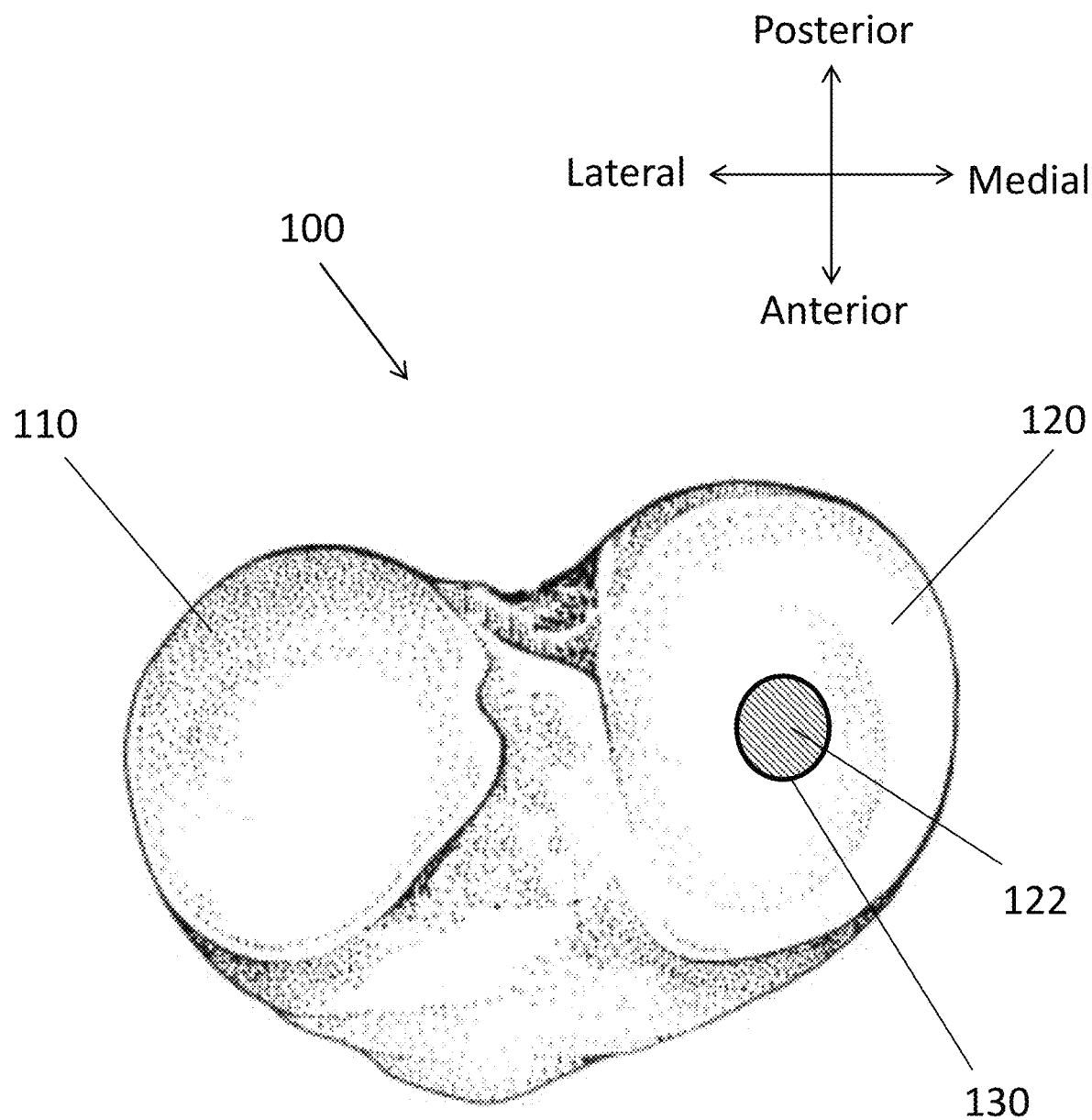
FIG. 3 is a representation of a bone density profile of the medial tibial condyle of the knee of FIG. 2.

A simplified top view of a tibia 100 of a healthy knee is illustrated in FIG. 2. As described above, the medial lateral meniscus sits atop the lateral tibial condyle 110 and the medial meniscus sits atop the lateral tibia condyle 120. During articulation of the femur against the tibia 100, the medial femoral condyle generally makes contact with the medial tibial sulcus 122, which is a concave groove centered on the superior surface of the medial tibial condyle 120. Because bone that experiences greater loading becomes denser than bone that experiences less loading, the density profile of the healthy medial tibial condyle 120 generally includes a relatively high density region 130 at the medial tibial sulcus 122, as shown in FIG. 3.

Figure 4:
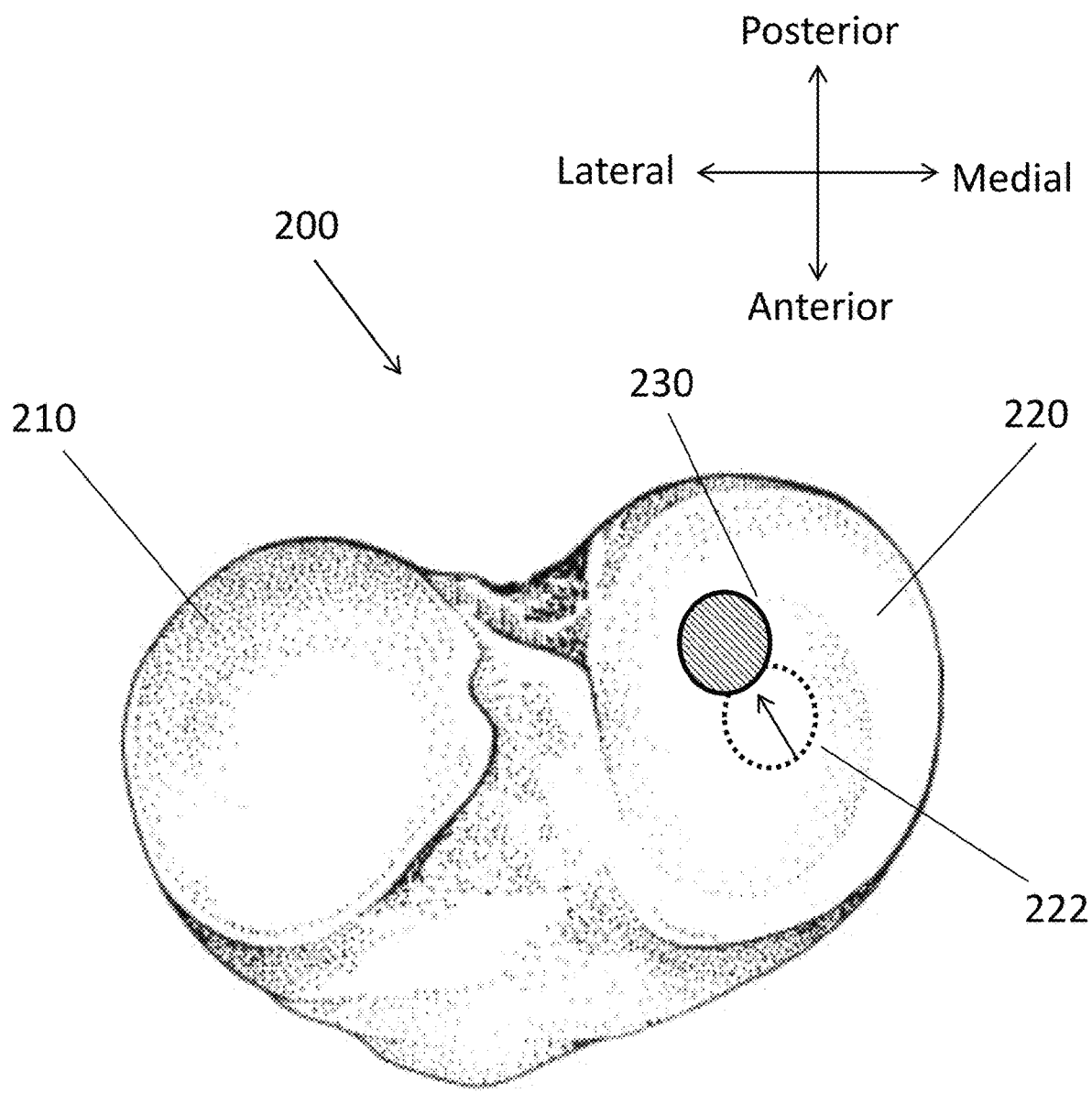
FIG. 4 is a representation of a bone density profile of a medial tibial condyle of a first unhealthy knee.
Figure 5:
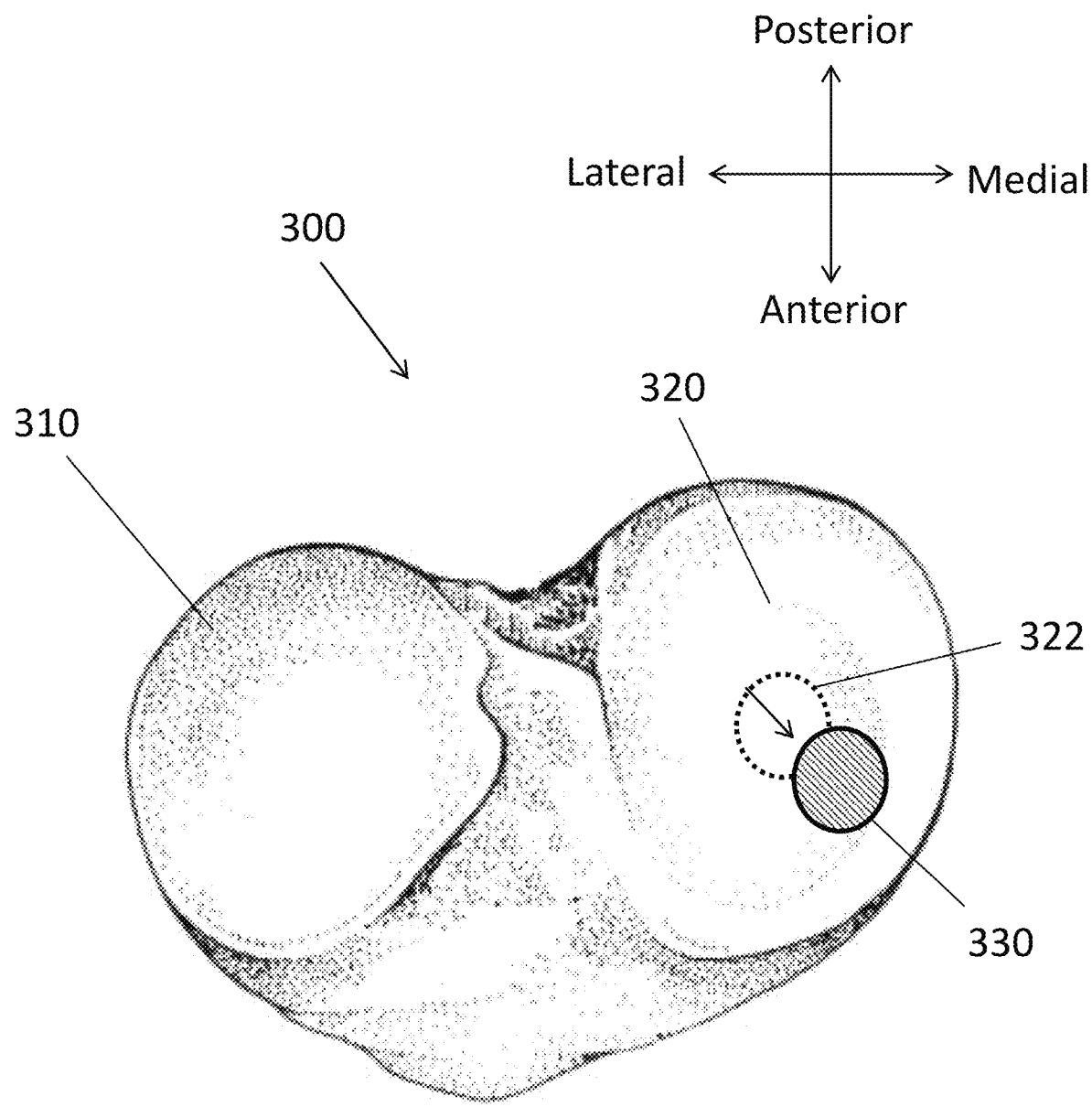
FIG. 5 is a representation of a bone density profile of a medial tibial condyle of a second unhealthy knee.

It has been found that in patients with a deficient ACL, the density profile (or density map) of the medial tibial condyle is non-aligned or shifted relative to what is seen in a typical healthy patient. For example, a top view of a tibia 200 of an unhealthy knee is illustrated in FIG. 4. The density profiles of one or both of the lateral tibial condyle 210 and medial tibial condyle 220 are different than what is seen in the healthy patient. For example, a deficient ACL may result in a patient's femur loading the tibia 200 at a location posterolateral of the medial tibial sulcus 222. Over time, this shift in loading will cause the bone to remodel and thus the density profile of the medial tibial condyle 220 to correspondingly shift. In particular, when the femur loads the medial tibial condyle 220 in a position posterolateral of the medial tibial sulcus 222, an area of relatively high bone density 230 may be seen in a position posterolateral of the medial tibial sulcus 222. In other words, a longitudinal axis extending through an area of relatively high bone density 230 is offset from a longitudinal axis extending through an area of relatively high bone density 130 shown in FIG. 3. Based upon the shift in loading, the general area of region 130 may not only shift to region 230 but may change in shape such that the area of region 230 is smaller, larger and/or has a perimeter that does not correspond to region 130. Another tibia 300 of an unhealthy knee is shown in FIG. 5. The density profiles of one or both of the lateral tibial condyle 310 and medial tibial condyle 320 are different than what is seen in the healthy patient. However, contrasted to the tibia 200 shown in FIG. 4, the tibia 300 of FIG. 5 shows an area of higher than expected bone density 330 in an anteromedial location compared to the medial tibial sulcus 322. It should be noted that density profiles shown in FIGS. 3-5 are provided in a simplified format for purposes of clarity. In addition, the shifts in bone density profiles are illustrated in an exaggerated format for purposes of clarity. Relatively small shifts in bone density profiles, for example on the millimeter scale, may provide enough information to reliably predict the integrity of the patient's ACL. In addition, although FIG. 4 illustrates a posterolateral shift and FIG. 5 illustrates an anteromedial shift in the relatively high bone density area, it is possible that both shifts may simultaneously occur relative to the sulcus, which may similarly indicate a loss in ACL integrity. Further, although the present disclosure focuses on shifting areas of relatively high bone density in the medial tibial condyle, it should be understood that shifts in relatively high bone density in the lateral tibial condyle may also be analyzed to facilitate diagnosing and/or determining the integrity of the ACL.

Information relating to shifts in bone density profiles of knees, and in particular the medial tibial condyle, may be utilized to non-invasively, accurately, and quantitatively predict the health of the ACL of a patient. This information may be used to inform the decision of what corrective procedure (including which prosthetic components), if any, should be performed on a patient. One example of this process is described in greater detail below in connection with FIGS. 6-7.

Prior to diagnosing a patient, a bone density profile model of the medial tibial condyle may be created. For example, a plurality of individual bone density profiles for patients with known ACL diagnoses may be entered into a database. The database may also include bone density profiles for patients with healthy ACLs. The bone density profiles may consist of images (e.g. x-rays, CT scans, etc.) or any other suitable form of data. The bone density profiles may be grouped by relevant categories including, for example, age group, ethnicity, male/female, and status of ACL (e.g. healthy, deficient AM bundle, deficient PL bundle, deficient AM and PL bundle, completely ruptured ACL, etc.). With enough examples of bone density profiles in the database, a relationship between bone density profiles and the expected ACL deficiency (if any) is created. For example, as shown in FIG. 3, a patient with a bone density profile in which the medial tibial condyle has the greatest density at the medial tibial sulcus 122 may be expected to have an ACL without deficiencies. On the other hand, patients that have the highest density regions of the medial tibial condyle shifted posterolaterally or anteromedially relative to the medial tibial sulcus may be expected to have a deficient ACL, with the type of deficiency being predicted by the particular bone density profile of the patient. In addition to the type of ACL deficiency, a quantitative indicator of the severity of the deficiency, e.g. on a scale of 1-10, may be output based on the bone density profile. The severity of the deficiency may also be quantified so that, depending on the value, a surgical procedure that spares the ACL or, on the other hand, a surgical procedure that sacrifices the ACL is suggested. For example, an ACL with relatively slight injury has the capability of returning to normal function and form if the ACL line of action and tension is restored through surgery using a suitable implant or set of implants as well as proper implant alignment. If the deficiency is so severe that return to normal function is unlikely or impossible, an ACL sacrificing procedure may be indicated by the quantitative indicator. It should be understood that although the bone density profile of a particular patient may be manually (or autonomously) compared to one or more bone density profiles of other patients with known ACL deficiencies, an alternative is to create a statistical (or other) model in which bone density information of a particular patient may be input into the model, the model being based on information derived from the database of bone density profiles of other individuals, and the model may output a diagnosis regarding the expected particular ACL deficiency of the patient. It should further be understood that although CT and other three-dimensional scans may provide for a relatively large amount of information, bone density (and bone density profiles) may be determined based solely on simple x-rays, such as an anterior-posterior ("AP") view x-ray. Using such an x-ray may be particularly desirable because of the relatively low dose of radiation compared to other types of imaging, and the simplicity of obtaining an x-ray of the relevant anatomy in the desired orientation compared to more complex imaging modalities.

Figure 6:
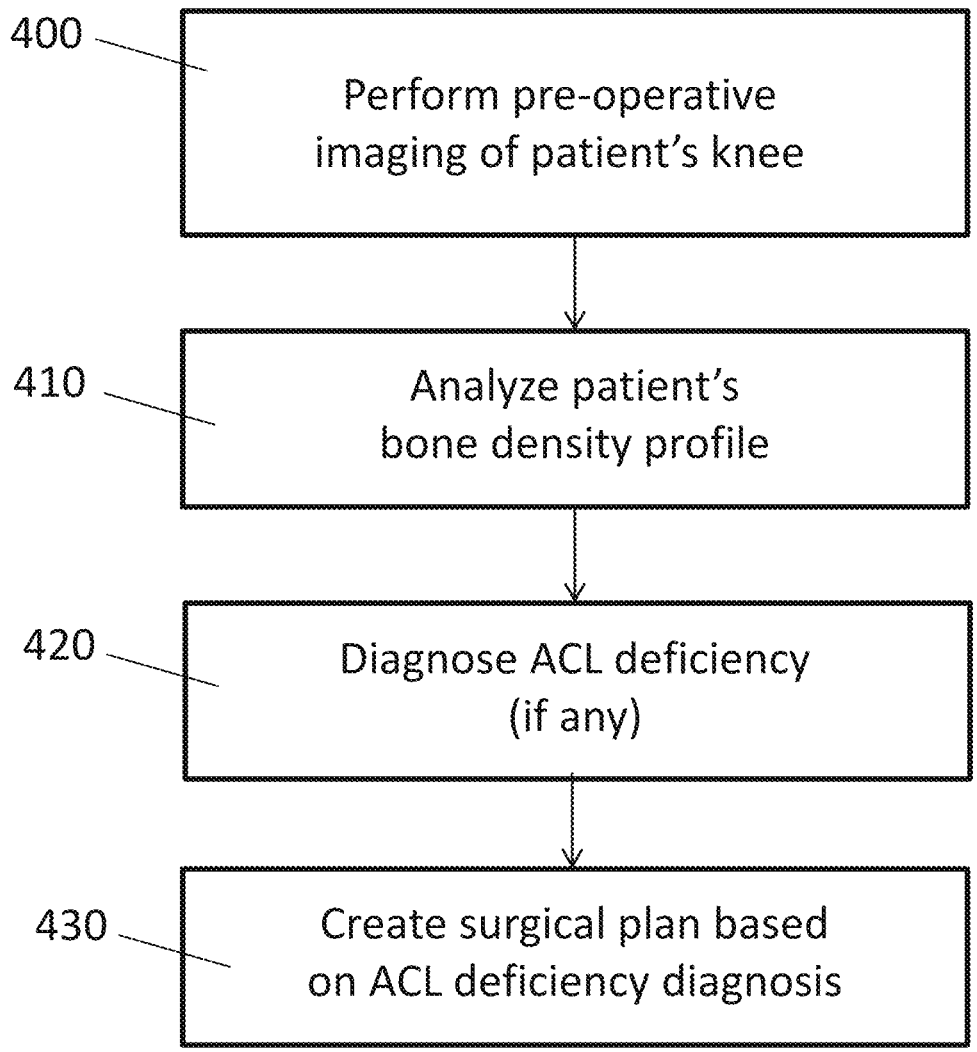
FIG. 6 is a flow chart of a method according to an aspect of the disclosure.
Figure 7:
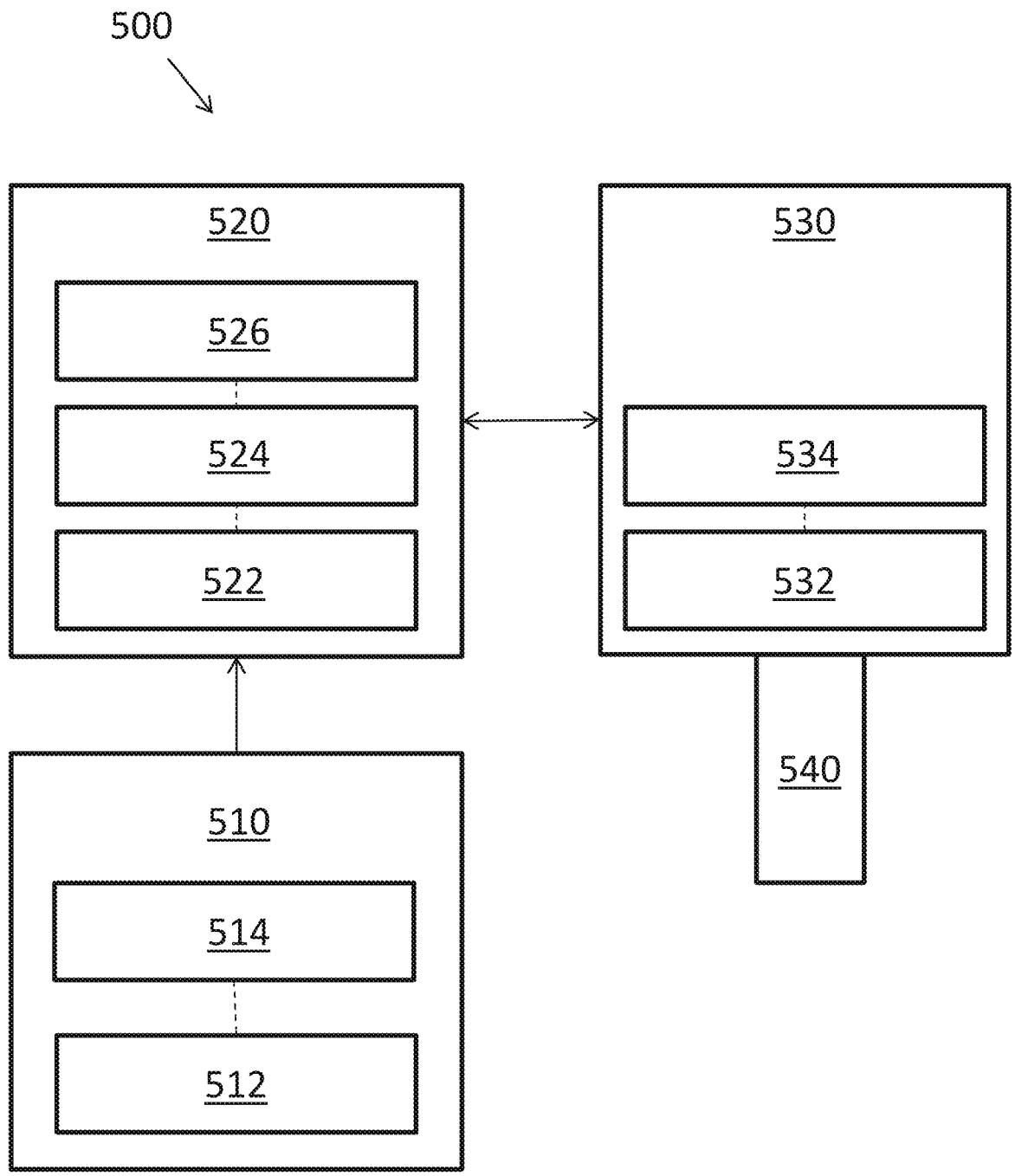
FIG. 7 is a schematic diagram of a system according to an aspect of the disclosure.

One example of a method of predicting ACL integrity and acting on that information, is shown in FIG. 6, with a system 500 of carrying out the method shown in FIG. 7. In a first step 400, one or more pre-operative images of the patient's knee are generated. The imaging may be carried out using any suitable imaging modality, including CT scanning, x-ray imaging, and/or others. The images of the knee may be stored in memory 512 of a first computer system 510. A processor 514 in computer system 510 may be operatively connected to memory 512 to analyze the bone density profile of the knee images stored in memory 512 in step 410. The bone density analysis may be performed according to known methods, for example by converting Hounsfield Units ("HU") of a CT image to bone mineral density values. U.S. Patent Publications No. 2015/0119987 and 2015/0080717, which are both hereby incorporated by reference herein, describe methods for mapping bone density. The one or more bone density profiles created may be transferred by any suitable means to a second computer system 520. However, it should be understood that a single computer system may be used or more than two computer systems as desired. It should also be understood that bone density may be analyzed in terms of absolute bone density and/or relative bone density. When determining absolute bone density, a calibration step may be performed with a medical image and/or scan including a bone mineral density phantom or any other suitable means. Relative density, on the other hand, may be analyzed based on, for example, voxel brightness within a CT scan. Relative bone density may be preferable for determining where relatively dense bone is located, but absolute bone density analysis may be necessary to determine the amount of loading on the ACL and to determine if quantitative density of the bone.

In step 420, the ACL deficiency (or lack thereof) of the patient is diagnosed. Computer system 520 may be utilized for the diagnosis. In particular, computer system 520 may include a memory module 522, a bone density profile model and/or database 524, and a processor 526, each of which may be operatively connected to one another. It should be understood that although represented as three modules, memory 522, bone density profile model and/or database 524, and processor 526 may comprise fewer or more modules as desired. The patient's bone density profile previously uploaded to computer system 520 may be compared to information in the bone density profile database 524 in order to diagnose the patient's ACL deficiency. For example, and as noted above, a user may complete this step manually by viewing the patient's bone density profile and comparing to bone density profiles of similar patients (e.g. selected by sex, age, race, etc.) visually on a display device. Preferably, the deficiency diagnosis is a completely or at least partially automated process. When using a bone density profile model 524, for example, information from the patient's bone density profile may be input into the model 524, with the output being a diagnosis of the patient's ACL deficiency, if any exists, which may include a quantitative description of the severity of the deficiency. The diagnosis may alternately be performed autonomously without a statistical model. For example, information relating to the patient's bone density profile may be compared to bone density information of other patients, preferably a relevant subset of patients, stored in database 524 with the aid of processor 526 to determine what deficiency exists in the patient's ACL, if any.

Based on the diagnosis of the patient's ACL integrity from step 420, the surgeon may then create a surgical plan based, at least in part, on the diagnosis in step 430. This step may be performed completely manually or partially or completely autonomously. For example, if a quantitative scale is used, a relatively high score that indicates a relatively high deficiency may indicate a total knee replacement ("TKR") in which the ACL is removed. A relatively low score that indicates a relatively slight deficiency may indicate a BCR implant system or a UKR procedure. A UKR procedure may be appropriate with a healthy (or relatively healthy) ACL, but if the bone density has shifted, fixation of a UKR implant system may be difficult, in which case a BCR implant system may be recommended. A robotic surgical system 530, which may be utilized to carry out the surgical procedure, may include a memory module 532 and a processor module 534 operatively connected to one another. The diagnosis from step 420 may be uploaded to robotic surgical system 530 in any suitable manner. The robotic surgical system 530 may suggest a particular procedure to the surgeon, for example via a connected display device, based on the patient's ACL diagnosis. Images and/or 3D models of the patient's knee may be displayed by the robotic surgical system 530, along with models of one or more potential implants, allowing the surgeon to manipulate the models of the implants with respect to the model of the patient's bone to confirm the surgical plan or to otherwise create an alternative surgical plan if the suggested plan is unsatisfactory. Bone density information previously determined may also be displayed by robotic surgical system 530 to provide the surgeon the ability to consider a surgical plan in relation to the patient's bone quality. It should be understood that the computer systems 510, 520, and robotic surgical system 530 need not be provided in the exact formats described above, and the specific example given herein is provided for purposes of clarity. For example, a single computer system may perform all of the image analysis, diagnosis, and surgical planning steps, and the surgical plan ultimately created may be performed by a separate surgical robot operatively connected to the single computer system Once the surgical plan is created (or accepted or otherwise finalized), the surgeon may employ one or more end effectors 540 operable connected to the robotic surgical system 530 to carry out various portions of the surgical procedure, for example including resurfacing the proximal tibia and/or distal femur to prepare the bone to accept one or more prosthesis, and actual placement of the prosthetic components in a desired position and/or orientation. One such robotic surgical system 530 that may be utilized is described in greater detail in U.S. Pat. No. 8,095,200, the disclosure of which is hereby incorporated by reference herein.

The disclosure provided herein may provide additional avenues for diagnosing and determining the integrity of a patient's tissue such as the ACL. For example, medical personnel may create medical images of a patient at periodic intervals over time, including at times before any tissue injury is suspected. For example, a patient may have a knee joint imaged via any suitable imaging modality every year, every other year, every five years, etc. The medical image or images created when the patient is presumed to have a healthy ACL may be used to track bone density profiles of the specific patient over time. In other words, the earlier images provide bone density profile information to be used as a baseline. The bone density profile over time information for a specific patient may provide a number of benefits. First, a shift of bone density from baseline may be more clearly recognizable since baseline information of the healthy patient is available. Second, such a shift in bone density profile may be recognized relatively early, which may allow intervention at a time when the ACL is still capable of being preserved. Third, the baseline information may provide a target so that a surgical intervention may be planned with the goal of modifying the patient's joint anatomy to return the joint to the earlier state which resulted in the baseline bone density profile. Fourth, a patient's baseline density profile may be used to track progress and recovery back to the expected loading norm following intervention (such as prosthesis implantation) for purposes of, for example, tracking clinical outcomes.

Still further, densities, and particular density ratios, of certain anatomical landmarks of a tibia may be analyzed to further assist in the determination of the health of the ACL. The inventors analyzed a plurality of medical images of knees of Caucasian males (FIG. 8), Caucasian females (FIG. 9), Asian males (FIG. 10), and Asian females (FIG. 11). Each patient was selected from the Stryker Orthopaedics Modeling and Analytics system ("SOMA") database. In particular, each patient was selected based on patient characteristics that would be expected to correspond to a healthy knee, such as age and body mass index ("BMI"). The individual patients, who have been given arbitrary patient identifiers in FIGS. 8-11, were controlled for height (between 140-199 cm), weight (between 40-100 kg), age (21-55 years), body mass index ("BMI") (<30), sex (male or female), and race (Caucasian or Asian). Each patient's medical image was analyzed to determine maximum densities at the anterior tibia, the posterior tibia, and the tibial tubercle. The units provided in FIGS. 8-11 are Hounsfield value units, which generally correspond to bone density. However, due to scaling differences, ratios of Hounsfield values were calculated to normalize the data. In particular, as shown in FIGS. 8-11, the ratios calculated include: (1) the maximum posterior tibial density to the maximum anterior tibial density ("P/A ratio"); (2) the maximum tibial tubercle density to the maximum anterior tibial density ("T/A ratio"); and (3) the maximum posterior tibial density to the maximum tibial tubercle density ("P/T ratio"). These point clusters were selected from the locations known to be the anatomical attachment sites of the ACL, PCL, and the patellar tendon. Patients in FIGS. 8-11 with particularly high density ratios are shown with a stippled background, and the average density ratio and standard deviations were calculated for those patients separately in a "High Ratio" group.

As can be seen from the data presented in FIGS. 8-11, the standard deviations ("SD") for each density ratio for the group of Caucasian males (FIG. 8), the group of Caucasian females (FIG. 9), the group of Asian males (FIG. 10), and the group of Asian females (FIG. 11) is small. In other words, a male Caucasian individual with a healthy knee would be expected to have a P/A ratio of near 1.53, a T/A ratio of near 1.02, and a P/T ratio of near 1.49. A female Caucasian individual with a healthy knee would be expected to have a P/A ratio of near 1.18, a T/A ratio of near 1.03, and a P/T ratio of near 1.16. A male Asian individual with a healthy knee would be expected to have a P/A ratio of near 1.31, a T/A ratio of near 1.03, and a P/T ratio of near 1.28. A female Asian individual with a healthy knee would be expected to have a P/A ratio of near 1.32, a T/A ratio of near 0.99, and a P/T ratio of near 1.32. Even across the male and female and Caucasian and Asian data, a T/A ratio of near 1 (or slightly above 1) appears to be expected for an individual with a healthy knee, whereas a significant deviation from a T/A ratio of about 1 may indicate the ACL or other anatomy of the knee is injured or is otherwise unhealthy. It should be understood that the values provided in FIGS. 8-11 are exemplary, and different sub-groups of individuals may be expected to have different density ratios for healthy knee joints depending on the particular population of interest.

The data provided in FIGS. 8-11 may provide for an objective and relatively simple analysis of a patient's medical image (such as an X-ray, including a single AP X-ray, or CT scan or scan slice) to determine whether the maximum density ratios of the posterior tibia, the anterior tibia, and the tibial tubercle are within an expected healthy range for a given population set. In some embodiments, a maximum density ratio of any or all of the P/A ratio, T/A ratio, and P/T ratio outside the expected value may be indicative of an unhealthy knee. In other embodiments, the extent that the maximum density ratio of any or all of the P/A ratio, T/A ratio, and P/T ratio falls outside the expected range may provide an extent of the likely problem. For example, if a male Caucasian patient has a T/A ratio that varies from the 1.02 average value in FIG. 8, a physician may have a basis to determine that there may be a problem with the knee joint, with the extent of deviation from the 1.02 average indicating the extent of the problem, such as the type and severity of ACL impairment. It may also be possible to determine the type of impairment of the ACL based on which of the ratios deviate from an expected value, and by how much the ratios deviate from that expected value.

Referring back to FIGS. 3-5, it should be understood that additional information may be obtained from tibial bone density maps that may assist in diagnosing a condition. For example, females who are prone to hyperextending the knee generally encounter more anterior and medial loading of the femur onto the tibia, which may correspond to greater bone density in these areas. On the other hand, males who are prone to hyperextending the knee generally see additional loading only in the medial direction of the tibia. Thus, this information may be used to help explain deviations in a tibial bone density map and thus assist in diagnosing the condition of the knee joint.

Still further, medical images such as X-rays or CT scans may be used similar to the manner described above to help predict certain soft tissue deformities that relate to knee joint kinematics. For example, a number of foot types may correspond to knee joint kinematics, including high arch, talipes cavus, cavoid foot, and supinated foot type (e.g. instepper or outstepper). The tibia of an individual that is an instepper (which may correspond to a flat-footed patient) may be rotated internally when bearing the weight of the femur during a gait, which may result in a tibial bone density map that deviates from an individual that is neither an instepper nor an outstepper. On the other hand, an individual that is an outstepper (which may correspond to a high-arched patient), may similarly see a different variation in the tibial bone density map. Although these conditions may result in a change in tibial bone density profile, such conditions may not necessarily indicate a problem with the ACL (or other components of the knee joint). Thus, in addition to determining variations in bone density profile of a patient's tibia, information relating to a patient's foot type or reported step conditions may be used, at least in part, in a holistic analysis of variations in a patient's tibial bone density profile to determine the likelihood and type of injuries or pathologies to the patient's knee joint.

Still further, the change in the tibial bone density profile over time may provide valuable information for patients having undergone either a TKA or UKA. In other words, if a patient receives a knee implant, the tibial bone density profile may be mapped over time to determine what changes are occurring as a result of changes in knee kinematics after the implant procedure. If the tibial bone density profile shifts over time to a density profile that would be expected for a similar patient with a healthy knee joint, such a change may help confirm that the knee implant is functioning desirably. However, if the bone density profile is not shifting toward what would be expected of a similar patient with a healthy knee joint, or is even shifting farther away from what would be expected of a similar patient with a healthy knee joint, such changes may be indicative of a problem with the knee implant. This type of analysis may be especially useful for a patient that has undergone a UKA procedure. For example, in patients undergoing UKA procedures, the previously healthy tibial condyle may undergo bone density profile changes as a result of the implant that replaced the unhealthy condyle. In such situations, it may be determined that the UKA implant is either not performing satisfactorily and/or that the disease is moving to the previously healthy condyle, which situations may indicate a need for a replacement of the previously healthy tibial condyle. Still further, useful information may be determined from monitoring the changes in tibial bone density profile of a patient that has undergone an ACL-sparing knee replacement and has received a BCR implant. As noted above, a BCR implant may be used for a patient that has a suitably functioning ACL. Changes in tibial bone density after a BCR implant procedure may indicate, for example, that the ACL is not being properly engaged, or is otherwise not loading as would be seen in a healthy patient's ACL. In such situations, it may be determined that the ACL is being rendered mostly useless and there was no advantage in using a BCR as opposed to an ACL-sacrificing knee implant. This information may assist a physician or other medical personnel in determining what the next course of treatment—if any—should be.

The concepts described above generally relate to the use of bone density measurements for diagnostic purposes, which in turn may assist a surgeon in choosing a particular type of intervention and to determine the effectiveness of the intervention. However, these concepts may be used and expanded upon to perform pre-operative virtual ligament balancing in order to choose a particular implant and to determine a desired position of the implant relative to the patient's bone to help ensure that the knee is properly stabilized by the soft tissue in flexion, extension, and in mid-flexion positions between flexion and extension. As noted above, gap balancing is traditionally performed intra-operatively, resulting in various limitations. By using the concepts described herein, the gap balancing may be performed virtually prior to making any incisions in the patient, providing a greater likelihood that the prosthetic implant procedure will be effective without the need for intra-operative modifications to achieve the desired gap balancing. It should be understood that although the present method is described in relation to a corrective knee procedure, the inventive concepts described herein may be applied to other joints with similar outcomes.

One data set that may be used in this method is bone density profiles, locations of contact between the femur and the tibia, and ligament positions in individuals with normal or healthy knees. This data may be obtained from images or sets of images, such as CT scans or other medical images, and may be obtained from databases or the like, such as the SOMA database described above. It should be understood that the disclosure provided herein may reduce or eliminate the need to consider imaging/scanning parameters, for example because the density calculations are not affected by the particular pose a patient is in during imaging. The objective of obtaining data with respect to normal or healthy knees is to determine how the bone density profiles and locations of contact relate to tension and laxity of the ligaments of the knee. For example, ratios based on the maximum HU values, similar to the description provided above in connection with FIGS. 8-11, may be use to normalize the measurements for all patients. In other words, each data pair may be in the form of a ratio so that the ratio of two values in one patient may be compared to the ratio of the same two values in another patient, which substantially or completely eliminates the importance of the quality (or other variable parameters) of the CT scan (or other imaging modality) used. The data pairs may be similar to those described above, for example the P/A ratio, the T/A ratio, or the P/T ratio. Other data points may include the maximum HU values at the MCL or LCL attachment sites, or the attachment sites of any other ligaments. Maximum HU values at contact points may also be transformed into ratios for comparison with other patients. For example, the ratio of the maximum HU value of the point on the medial tibial plateau which is contacted by the medial femoral condyle to the maximum HU value of the point on the lateral tibial plateau which is contacted by the lateral femoral condyle may be a ratio to be compared between patients. Still further, ratios may be used to normalize the contact locations as well. For example, the centroid of the density boundary of the medial tibial contact location may be determined, which may be referred to as the medial contact or medial contact point. The distance from the medial contact point to the posterior medial tibial plateau (CP) may be divided by the anterior-to-posterior length of the medial tibial condyle to determine a medial centroid to AP length ratio (MSPT). Similarly, the distance from the medial contact point to the center of the medial tibial plateau (CM) may be divided by the distance from the center of the medial tibial plateau to the medial edge of the tibial plateau (which may be referred to as Medial Width) to determine a medial centroid to medial width ratio (MSMT). By using these types of ratios, contact locations may be normalized between different patients for comparison.

The tension and laxity of the knee ligaments for these normal or healthy knees may be another data set in the group. The tension and laxity of the knee ligaments may be determined, for example, by cadaveric testing in which tools such as torque wrenches or the like are used to physically measure how tense or lax particular knee ligaments are. For example, ligaments of a cadaver may be sequentially cut using a dial test to determine the contribution of each ligament to knee stability. These two datasets may be compared to correlate the relationship between bone density profiles and locations of contact to the amount of tension or laxity in the various knee ligaments. These correlations may be determined for various populations or sub-populations, including age group, sex, ethnicity, etc.

With the knowledge of what the ratio of bone density to ligament tension should be in a patient with a normal or healthy knee, which may be determined from the first two datasets, an equilibrium equation may be created with tension and compression forces balancing one another. This equation may be solved for the healthy knees (the optimum scenario) and a particular patient's knee (the encountered scenario), with parameters in the equation of the encountered scenario being varied to determine what the implant positioning should be in order to achieve a desired result similar to the encountered scenario. As is described in greater detail below, certain parameters may be weighted as more or less important than other parameters when solving for the encountered scenario, as a physician may determine that certain ones of the parameters are more important to the ultimate solution than other ones of the parameters. In other words, the solution of the equation is essentially an optimization problem which may not result in a single perfect solution for each relevant parameter, but rather a set of parameters that most closely result in a match to the healthy patient. Because certain of the parameters may be determined to be more important by a physician, those parameters may be more heavily weighted in the optimization equation.

Figure 12:
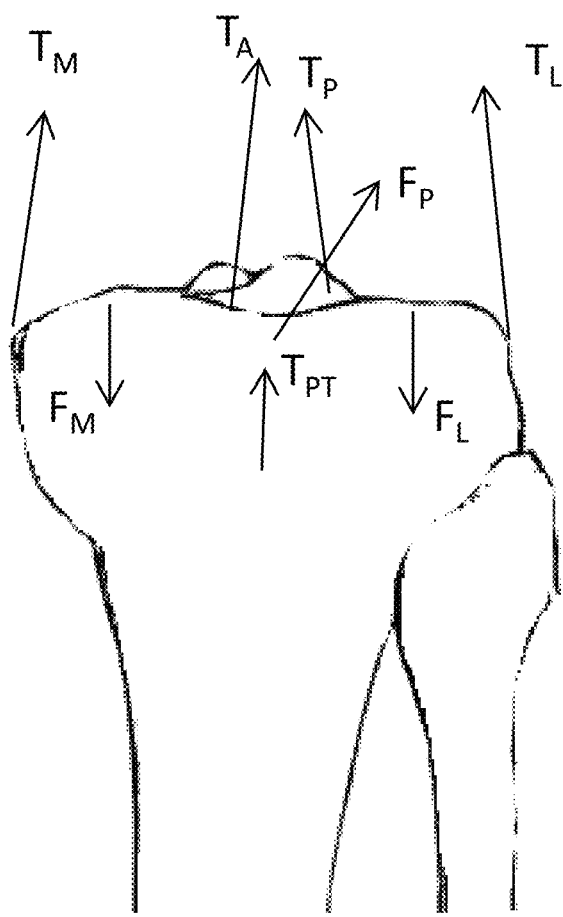
FIG. 12 is a schematic diagram of forces acting on a proximal tibia in the coronal plane.

FIG. 12 is a simplified illustration of the left proximal tibia illustrating the tensile and compressive forces acting on the tibia in the coronal plane. In particular, five tensile forces and two compressive forces are illustrated. The five tensile forces include the ACL tensile component $T_A$, the PCL tensile component $T_P$, the MCL tensile component $T_M$, the LCL tensile component $T_L$, and the tubercle attachment tensile component $T_{PT}$. The two compressive components include the medial femoral condyle compressive component $F_M$, and the lateral femoral condyle compressive component $F_L$. The femur similarly has a plurality of forces acting on it, including the four tensile components (ACL, PCL, LCL, MCL tension) and three compressive components (medial condyle, lateral condyle, and patellofemoral ("PF") compressive force. It should be understood that a PF compressive force is not illustrated on the tibia in FIG. 12, as the resultant of the PF force on the tibia is $T_{PT}$.

The forces acting on the knee joint must balance out or sum to zero, which provides a first equation for vertical loads and a second equation for horizontal loads acting on the knee. In the coronal plane, the vertical tensile forces equal the vertical compressive forces. One exemplary equation for balancing out vertical forces in the coronal plane is provided below, although it should be understood that other equations incorporating more complex soft-tissue structures and interactions may be included in such a balancing equation:

$$T_M \cos\theta_M + T_A \cos\theta_A + T_P \cos\theta_P + T_L \cos\theta_L + T_{PT} \cos\theta_{PT} = F_M \cos\theta_{FM} + F_L \cos\theta_{FL}$$

Similarly, in the coronal plane, the horizontal forces must sum to zero, providing the following second exemplary equation, although it should be understood as above that more complex soft-tissue structures and interactions may be included in such a balancing equation:

$$T_M \sin\theta_M + T_A \sin\theta_A + F_M \sin\theta_{FM} = T_P \sin\theta_P + T_L \sin\theta_L + T_{PT} \sin\theta_{FT} + F_L \sin\theta_{FL}$$

Figure 13:
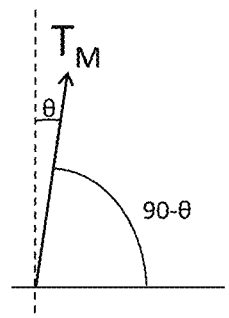
FIG. 13 is a diagram showing the angle of a particular force from FIG. 12.

In the two equations provided above for the coronal plane calculations, the convention of the angles of the forces is illustrated in FIG. 13, which shows in particular the angle of the tensile force provided by the MCL.

In addition to the balancing of the vertical and horizontal forces acting on the knee in the coronal plane, a third equation may be utilized to resolve the moments acting in the coronal plane. The equation for resolving the moments in the coronal plane may be provided as follows:

$$T_M \cdot d_1 + T_A \cdot d_A + F_L \cdot d_4 = F_M \cdot d_3 + T_{PT} \cdot d_{PT} + T_L \cdot d_2 + T_P \cdot d_P$$

Figure 14:
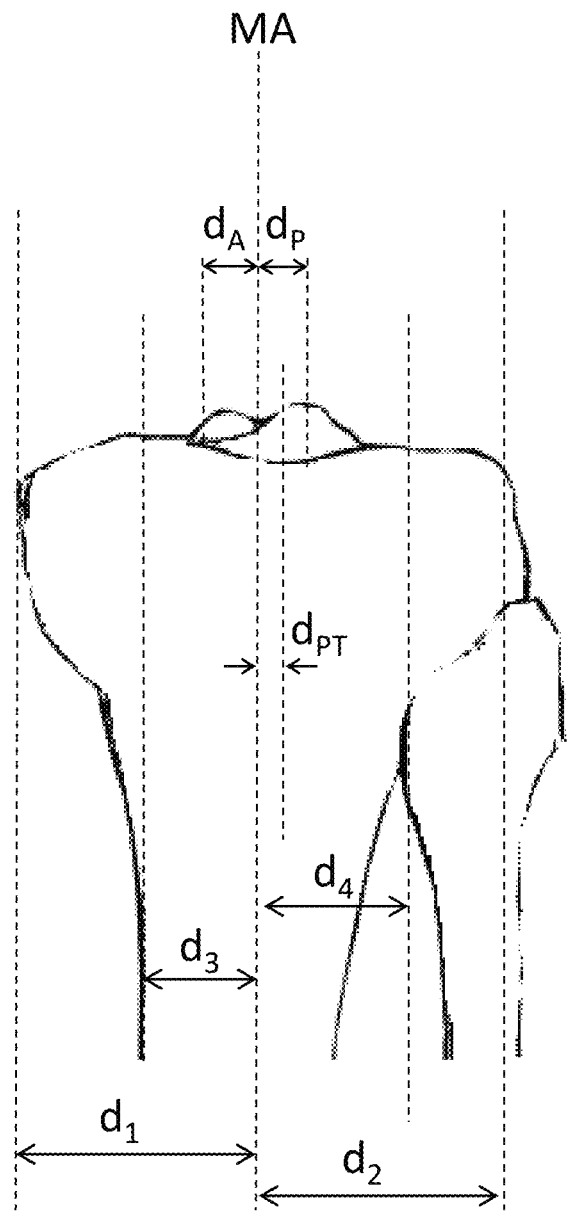
FIG. 14 is a schematic diagram of distances at which the forces of FIG. 12 act on the proximal tibia.

Although one particular example of a moment balancing equation is provided above, it should be understood that other soft-tissue structures may be accounted for to provide in a more complex equation than the simplified version provided above. FIG. 14 illustrates an example of the distances used in the equation above for balancing the moments in the coronal plane. The moments may be balanced about the mechanical axis MA, for example as determined form the center of the tibia to the center of the hip joint. Distance $d_1$ is the horizontal distance between the mechanical axis MA and the point of attachment of the MCL to the proximal tibia. Distance $d_2$ is the horizontal distance between the mechanical axis MA and the point of attachment of the LCL to the proximal tibia. Distance $d_3$ is the horizontal distance between the mechanical axis MA and the position of the medial tibial sulcus in which the medial femoral condyle sits. Distance $d_4$ is the horizontal distance between the mechanical axis MA and the position of the lateral tibial sulcus in which the lateral femoral condyle sits. Distance $d_A$ is the horizontal distance between the mechanical axis MA and the point of attachment of the ACL to the proximal tibia. Distance $d_P$ is the horizontal distance between the mechanical axis MA and the point of attachment of the PCL to the proximal tibia. Distance $d_{PT}$ is the horizontal distance between the mechanical axis MA and the point of attachment of the patellar ligament to the tubercle attachment site. It should be understood that, in the moment balancing equation provided above, the forces should be resolved to their horizontal and vertical components to calculate the horizontal and vertical moments, similar to the equations above directed to balancing of horizontal and vertical forces. Still further, it should be understood that the equation(s) for the resolution of the forces based on these distances is only used for the encountered scenario (i.e. the particular patient at issue that is to be treated). In other words, the representative healthy data set (i.e. the optimum scenario) is associated with known ratios, and computer software may be used to solve the appropriate dwell point and ratios to reflect the dimensions of the particular patient. As an example, if the particular patient's distance $d_1$ is 40 mm, the healthy dataset ratios will be solved for medial and lateral condyle dwell points with the 100% medial distance being 40 mm, and finding a corresponding dwell point calculated as 60% of that (24 mm for that specific patient). The ratios used for implementing this may be based, for example, on the MSMT ratio described above.

An equation for relating the stress and strain of the ligaments may be provided as follows:

$$\sigma(t) = \left[\int_0^\tau E(t-\tau)\frac{d\varepsilon(\tau)}{d\tau}d\tau\right] + E_{inst.relax}\varepsilon(t)$$

In the above equation, stress is represented by $\sigma(t)$ and strain is represented by $\varepsilon(t)$, with $E(t)$ representing the relaxation function with time (t), $\tau$ representing the time variable of integration, and $E_{inst.relax}$ representing instantaneous creep and relaxation. The above equation may be used in order to correlate the density (or HU value) ratios to the tension/laxity values of ligaments determined from the cadaveric testing and/or values determined from published literature. In other words, it is known that ligaments behave according to the equation provided above for stress/strain. The ligament tensioning may be determined based on this equation, and the determined stress may be related to the footprint tensions. This correlation may only need to be performed a single time for validation purposes. Once the validated model is generated of ratios of density (or HU values) to ratios of stress/strain, the appropriate density (or HU) ratio for each individual patient may be calculated to restore the expected stress/strain for each ligament.

The total force acting on the knee $F_{total}$ may be calculated as half of the body weight BW, as each knee supports half the body weight. Generally, in the knee, the medial femoral condyle compressive component $F_M$ represents about 70% of the compressive load on the knee while the lateral femoral condyle compressive component $F_L$ represents about 30% of the compressive load on the knee. However, it should be understood that this ratio is not fixed, and generally the medial loading represents a larger portion of the force applied to the tibia compared to the lateral loading. The ratio can be validated from the healthy dataset and enforced on the particular patient having corrective surgery in order to restore appropriate loading. This ratio is one of the parameters that me be solved for in the optimization problem, and thus may not be restored perfectly as ligament tensions and implant positions will also have an effect on the overall loading. However, this is a parameter the surgeon may prefer to give more or less weight to depending on the particular situation of the individual patient.

The above equations may be used to correlate the known tension and laxity of the ligaments of healthy knees to the known bone density profiles of the healthy patients. It should be understood that although equations are presented above for the coronal plane, in practice the corresponding equations for the sagittal and axial planes would be used as well to solve the equilibrium equation in all three dimensions. Solving in three dimensions may involve slightly more complexity than solving in a single dimension as described above, but given the disclosure provided herein, a person of skill in the art would understand how to solve the three-dimensional problem based on the disclosure of solving the one-dimensional problem provided above. For example, vector calculations using a 3D polar coordinate system may solve for forces in all three planes simultaneously. Still further, the mechanical axis MA is used above as an example and other approaches may be used for the optimization method, including the anatomical axis, based on the preference of the physician.

The above correlation may be determined for groups of sub-populations with healthy knees. For example, these correlations may be provided for patients with particular characteristics, such as age group, sex, and ethnicity. When generating a correction plan for a particular patient with an unhealthy knee, the relevant correlation corresponding to the patient's subgroup characteristics may be used to optimize the positioning of the implant as described below. As noted above, rather than using absolute values for density (or HU values) and relevant distances, ratios may be used to reduce or eliminate patient-to-patient variation. However, subgroups may still exist for different parameters that can be grouped based on machine learning principles. In other words, the system can look for correlations of clusters for each dataset and determine if all patients fit in one group for a parameter or if there is variation causing more than one cluster. This may be particularly useful for the vector analysis where more than one group may be expected since lax and tight ligaments can exist in the healthy patients.

In order to generate a correction plan for a patient with an unhealthy knee, CT or other medical images or scans may be performed on the particular patient. The CT scans may be uploaded to software that may be running on computer system 520 described above or any other similar computer system accessible by the surgeon. The software may utilize the equations provided above, as well as the correlation determined for patients with healthy knees (and preferably for the correlation determined for the subgroup most relevant to the particular patient), to solve for the medial and lateral loading on the knee and the tensions from the patient's ligaments. The software may also analyze the sites of ligament attachment and the dwell points of the medial and lateral condyles to determine ligament laxity, and use the various density and distance ratios described coupled with the contacts locations to solve for femoral, tibial, and patellar positioning, preferably in three dimensions, to optimize all the parameters in the patient to match as closely as possible to the corresponding subgroup with healthy knees. In other words, the optimal positions of contact in three dimensions of the femoral condyles with the corresponding tibial sulcus may be determined using software implementing the above equations for the particular patient, so that the positioning of the implant results in ligament tensions that are balanced, preferably not just in flexion and extension, but in mid-flexion ranges as well.

As noted above, during the procedure for corrective planning, the surgeon may be able to weight certain parameters as more or less important than others when solving the optimization problem presented above. For example, a surgeon may use the software to pick a particular parameter or particular parameters and, depending on the influence of the chosen parameters on the other parameters, can handicap the non-chosen parameters by a percentage value in order to increase the convergence value for the chosen parameter(s). In one example, if a surgeon determines the flexion angle is important, the sagittal angle can be sloped more, which penalizes the ACL/PCL ratio but improves femoral roll back. If the priority is not flexion, for example which may be the case in elderly patients, the surgeon may prioritize varus/valgus alignment optimization to prevent bones stresses, as the elderly may have weaker bones, which may not be suitable for more aggressive varus/valgus angles that younger patients can tolerate.

After the surgeon has used the software on computer system 520 (or any other suitable computer system), either with or without prioritizing parameters as described above, the software outputs the desired position in three dimensions of the contact points between the femoral prosthesis and tibial prosthesis (or otherwise between any remaining native bone contact points with the desired prostheses if less than a total knee arthroplasty is being performed). Based on the information determined from patients with healthy knees in the sub-group or sub-groups most relevant to the particular patient, and based on the patient's particular anatomy as determined from the imaging described above, the output positions of the contact points between the femoral and tibial implants modify the encountered scenario (i.e. the patient's pre-operative condition) to mimic as closely as possible the optimum scenario (i.e. the healthy knee condition of the most relevant sub-group). As a result, by performing the surgery according to the plan determined by the software (including any additional input the surgeon may provide to supplement the software), the ligaments in the patient's knee should be desirable balanced in flexion, extension, and mid-flexion ranges if the implant is implanted according to the determined plan. Ligament balancing may be checked intraoperatively to confirm. If required, traditional intraoperative ligament balancing will still remain an option, but the likelihood of requiring additional ligament balancing will be significantly reduced based on the results of the virtual pre-operative ligament balancing described above.

Additional information regarding the laxity of ligaments, such as those in the knee, may be predicted using density values at different layers near the site of attachment of the particular ligament. For example, for the site of attachment for a particular ligament, the position or point of the bone with the greatest density may be determined in more than one layers. If the ACL is being examined, for example, two, three, or more layers or "slices" of bone density data may be analyzed to determine the direction of a vector passing through the points of maximum density. In other words, transverse cross-sections of the proximal tibia may be analyzed at the site of attachment of the ACL to the proximal tibia, for example at distances of 1 mm, although greater or lesser distances between individual slices or layers may be used. The point of maximum bone density in each layer may be determined, for example using any one of the computer systems or programs described above, and a line may be drawn or otherwise overlaid on an image of the bone (although the line may be otherwise drawn without using a backdrop of the bone), where the line passes through each point of maximum density in each slice or layer. It should be understood that the line may be a best-fit line as the particular data points may not all be positioned in a perfect line. In any event, the direction in which the vector line that passes through (or otherwise a best-fit line that passes through) the points of maximum density in the various layers of depth at the site of ligament attachment may help predict the amount of laxity in the particular ligament. For example, a vector line created using the methodology described above that points in the anterior direction may indicate that the ligament is relatively loose, compared to a vector line that is substantially vertical (i.e. substantially parallel to the anatomical axis of the tibia). It should be understood that, although two particular examples are given above (i.e. relatively loose with an anterior-pointing vector, relatively stiff with a vertical pointing vector), the predicted stiffness of the ligament may be determined to be more stiff when the vector is closer to vertical, and more loose when the vector is closer to anterior-pointing. Further, although one specific knee ligament is described above as an example, similar analysis may be performed with other knee ligaments.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of preoperatively planning a knee arthroplasty, comprising:
    obtaining, by one or more processors, a medical image of a patient's knee joint;
    determining, by one or more processors based on the medical image, a patient bone density profile associated with a medial tibial condyle, the bone density profile being based on a bone density at two or more locations on the medial tibial condyle, each of the two or more locations being associated with a knee joint soft tissue attachment site;
    automatically determining, by one or more processors based on the patient bone density profile and one or more bone density profiles stored in memory, an ACL deficiency metric; and
    identifying, by the one or more processors based on the ACL deficiency metric, an ACL sparing or an ACL sacrificing knee implant system; and
    outputting, by the one or more processors, the identified ACL sparing or the ACL sacrificing knee implant system.

2. The method of claim 1, wherein the automatically determining step includes comparing the patient bone density profile to a reference bone density profile.

3. The method of claim 1, wherein the obtaining step includes obtaining a plurality of image layers associated with the medical image.

4. The method of claim 3, wherein the determining step includes identifying a position of maximum bone density in each of the plurality of image layers.

5. The method of claim 4, wherein the automatically determining step includes determining the position of the maximum bone density relative to an expected position of maximum bone density.

6. The method of claim 5, wherein the expected position of maximum bone density is determined by reference bone data stored on a database.

7. The method of claim 1, wherein in the ACL sparing implant system is a bicruciate retaining implant system, and the ACL sacrificing knee implant system is a total knee arthroplasty system.

8. The method of claim 1, further comprising updating the planning of the knee arthroplasty by including the ACL sparing or the ACL sacrificing knee implant system for implantation in the patient.

9. A method of preoperatively planning a knee arthroplasty, comprising:

obtaining, by one or more processors, a medical image of a patient's knee joint;

determining, by one or more processors based on the medical image, a patient bone density profile associated with a medial tibial condyle;

automatically determining, by one or more processors based on the patient bone density profile and one or more bone density profiles stored in memory, an ACL deficiency metric; and identifying, by the one or more processors based on the ACL deficiency metric, an ACL sparing or an ACL sacrificing knee implant system; and outputting, by the one or more processors, the identified ACL sparing or the ACL sacrificing knee implant system;

wherein the identifying step considers an extent of a difference between characteristics of the patient bone density profile and a reference bone density profile.

10. The method of claim 9, wherein the ACL deficiency metric accounts for an offset of a maximum bone density region of the patient relative to a maximum bone density region of the reference bone density profile.

* * * * *